US00PP22451P3

(12) United States Plant Patent
Post et al.

(10) Patent No.: US PP22,451 P3
(45) Date of Patent: Jan. 10, 2012

(54) GRAPE PLANT NAMED 'PROPHECY'

(50) Latin Name: *Vitis vinifera*
Varietal Denomination: Prophecy

(76) Inventors: Mathew J. Post, Altus, AR (US); Thomas B. Post, Altus, AR (US)

( * ) Notice: Subject to any disclaimer, the term of this patent is extended or adjusted under 35 U.S.C. 154(b) by 0 days.

(21) Appl. No.: 12/592,709

(22) Filed: Dec. 1, 2009

(65) Prior Publication Data

US 2011/0131692 P1 Jun. 2, 2011

(51) Int. Cl.
*A01H 5/00* (2006.01)

(52) U.S. Cl. ..... Plt./205

(58) Field of Classification Search ..... Plt./205
See application file for complete search history.

*Primary Examiner* — Susan McCormick Ewoldt

(74) *Attorney, Agent, or Firm* — Andrus, Sceales, Starke & Sawall LLP

(57) ABSTRACT

The invention is a new and distinct variety of grape plant designated #194-95, "Prophecy", which produces small, round, blue-black colored fruit suitable for red wine production. It combines late bud-break and ripening, excellent disease resistance, extremely high vigor, moderate productivity, and good mechanical harvestability with high wine quality chemistry and excellent flavors.

7 Drawing Sheets

Latin name: *Vitis vinifera.*
Varietal denomination: 'Prophecy'.

BACKGROUND

Most grape varieties used for production of high quality wines around the world are of the species *Vitis vinifera*. However, varieties of *Vitis vinifera* are susceptible to phylloxera (*Daktulosphaira vitifoliae shimer*, formerly *Phylloxera vitafoliae filch* or *Phylloxera vastatrix planchon*,) the most widely known aphid or root louse. Because of its destruction of grapevines the world over, *Vitis vinifera*, in most areas, is normally grafted to *phylloxera*-tolerant rootstock to provide longevity and viability to grapevine plantings.

Grafting is time-consuming and expensive, and requires skilled labor. By creating a genetic cross of *Vitis vinifera* and phylloxera-tolerant vines, a hybrid may be realized which is tolerant to phylloxera and of high wine quality. The new hybrid may be reproduced by rooted cuttings and will require less specialized cultural practices to maintain in the vineyard, thereby reducing cost and labor to produce a high quality wine.

A new cultivar of grape, #194-95, called 'Prophecy' is described herein. The new cultivar originated from a hand-pollinated cross of 'Munson' (Jaeger No. 70-a *Vitis lincecumii-rupestris* hybrid)×'Cabernet Sauvignon' (*Vitis vinifera*-Clone No. 169) made in 1995. The resulting seedling vines were planted in a vineyard near Altus, Ark. in 1999.

The vines fruited in 2001 and one vine, designated #194-95, was selected for its excellent plant health, extreme vigor, excellent fruit flavor and late season ripening.

This new hybrid is late to ripen. Vintners and grape growers desire varieties that differ in ripening time so that the harvest labor and equipment, and vinification facilities are optimally utilized. A later-ripening red wine grape would result in enhanced ease of vinification because the climate is cooler during the later season, and would naturally be of great economic value to vintners.

SUMMARY OF THE INVENTION

This new and distinctive cultivar of grape originated from a hand pollinated cross of 'Munson' (Jaeger No. 70-a *Vitis lincecumii-rupestris* hybrid)×'Cabernet Sauvignon' (*Vitis vinifera*-Clone No. 169) made in 1995 at a vineyard located near Altus, Ark. (West-Central Arkansas). 'Munson' was used as the female parent and 'Cabernet Sauvignon' Clone No. 169 was used as the male parent.

The seeds resulting from this controlled hybridization were germinated in a garden on a vineyard property near Altus Ark. in 1996. The vines produced from these seeds were fruited during the growing season of 2001 and one seedling vine, designated Post 194-95, was selected for its excellent plant health, extreme vigor, and excellent fruit quality for wine and late season ripening.

During 2002 the original plant selection was propagated asexually from hard wood cuttings, at the above noted location, and a test row of 25 plants was established in 2003. Subsequently, a larger planting has been established in 2006 at the same location.

During all asexual multiplications, the characteristics or the original plant have been maintained and no aberrant phenotypes have appeared.

The new cultivar has been named the 'Prophecy' cultivar.

BRIEF DESCRIPTION OF THE PHOTOGRAPHS

The accompanying photographs show typical specimens of the new variety in color as nearly true as it is reasonably possible to make in a color illustration of this character.

DETAILED DESCRIPTION OF THE NEW CULTIVAR 'PROPHECY'

Figure 1:
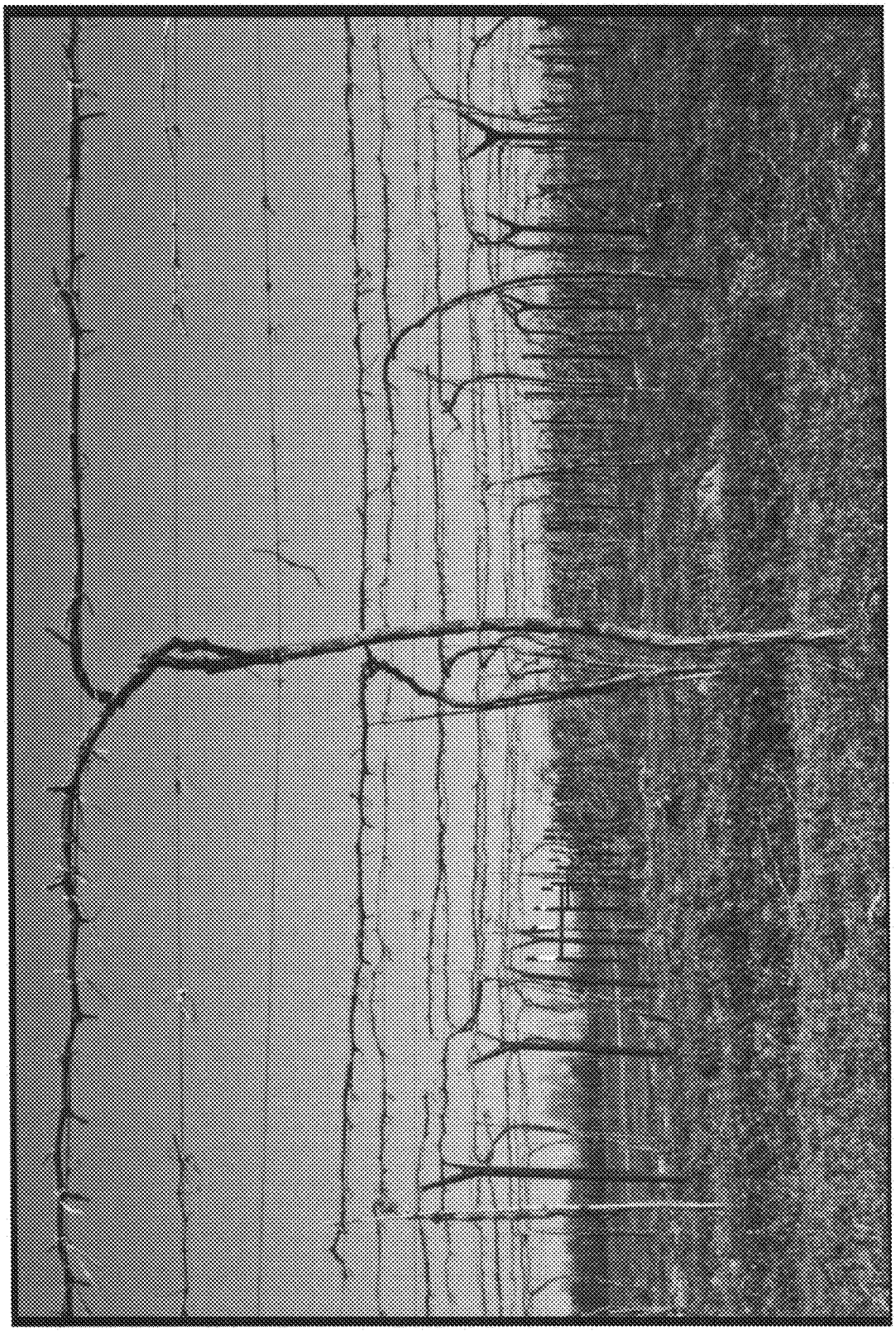
FIG. 1 is a photograph showing a grape plant of the cultivar 'Prophecy' in dormancy.
Figure 2:
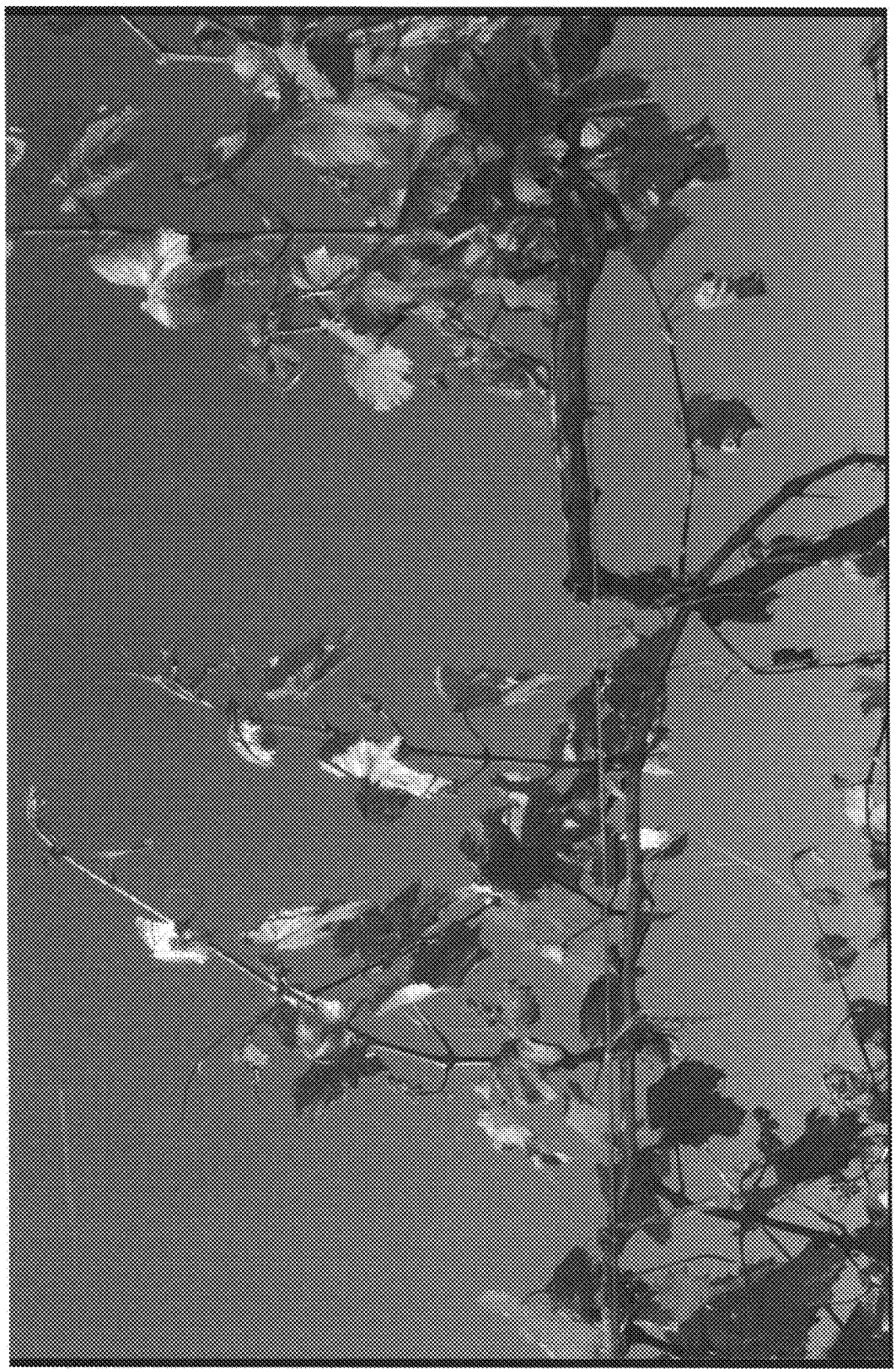
FIG. 2 is a photograph showing the grape plant prior to bearing fruit.
Figure 3:
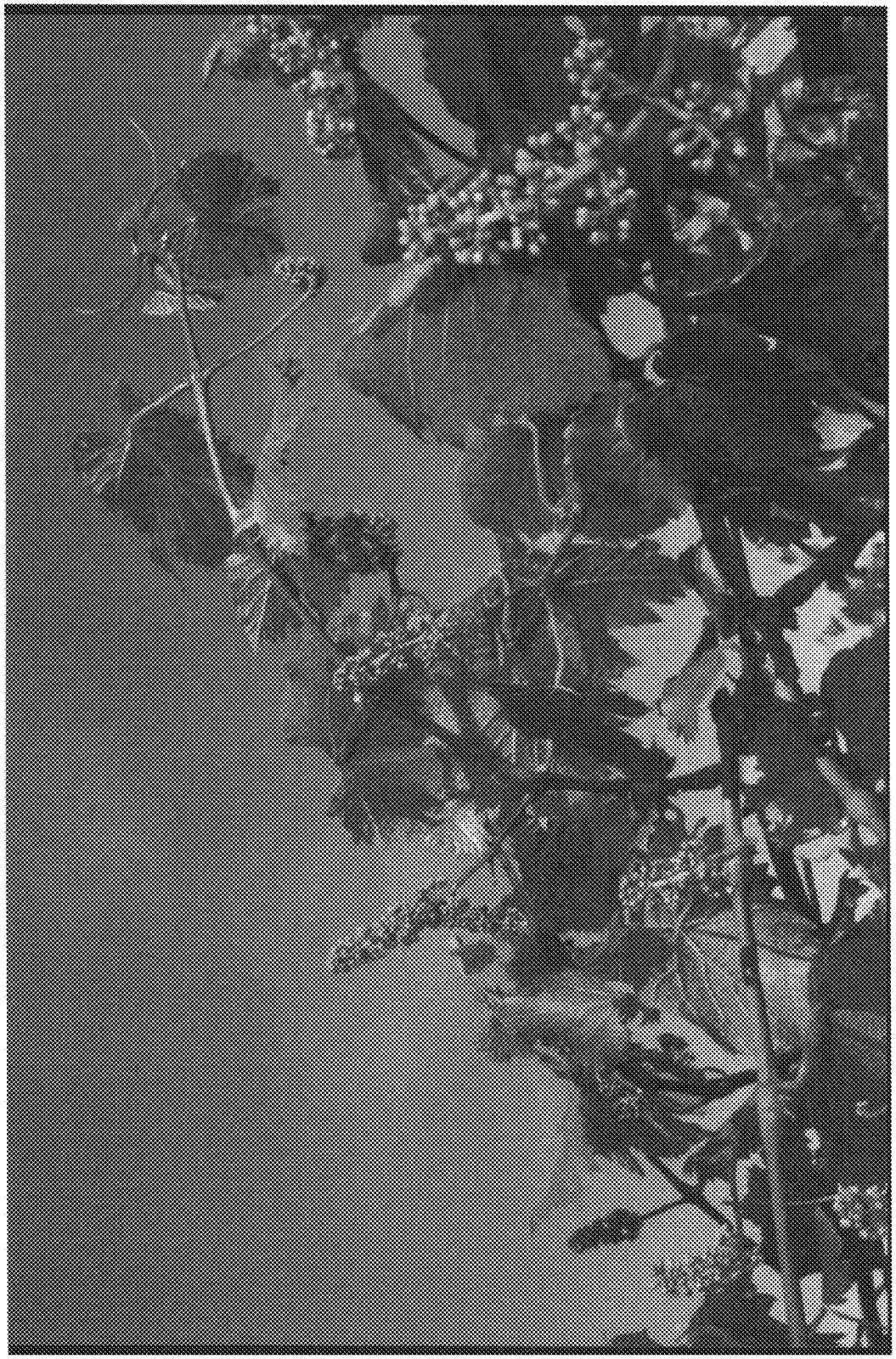
FIG. 3 is a photograph showing fully expanded rachis at pre-bloom (flower buds).
Figure 4:
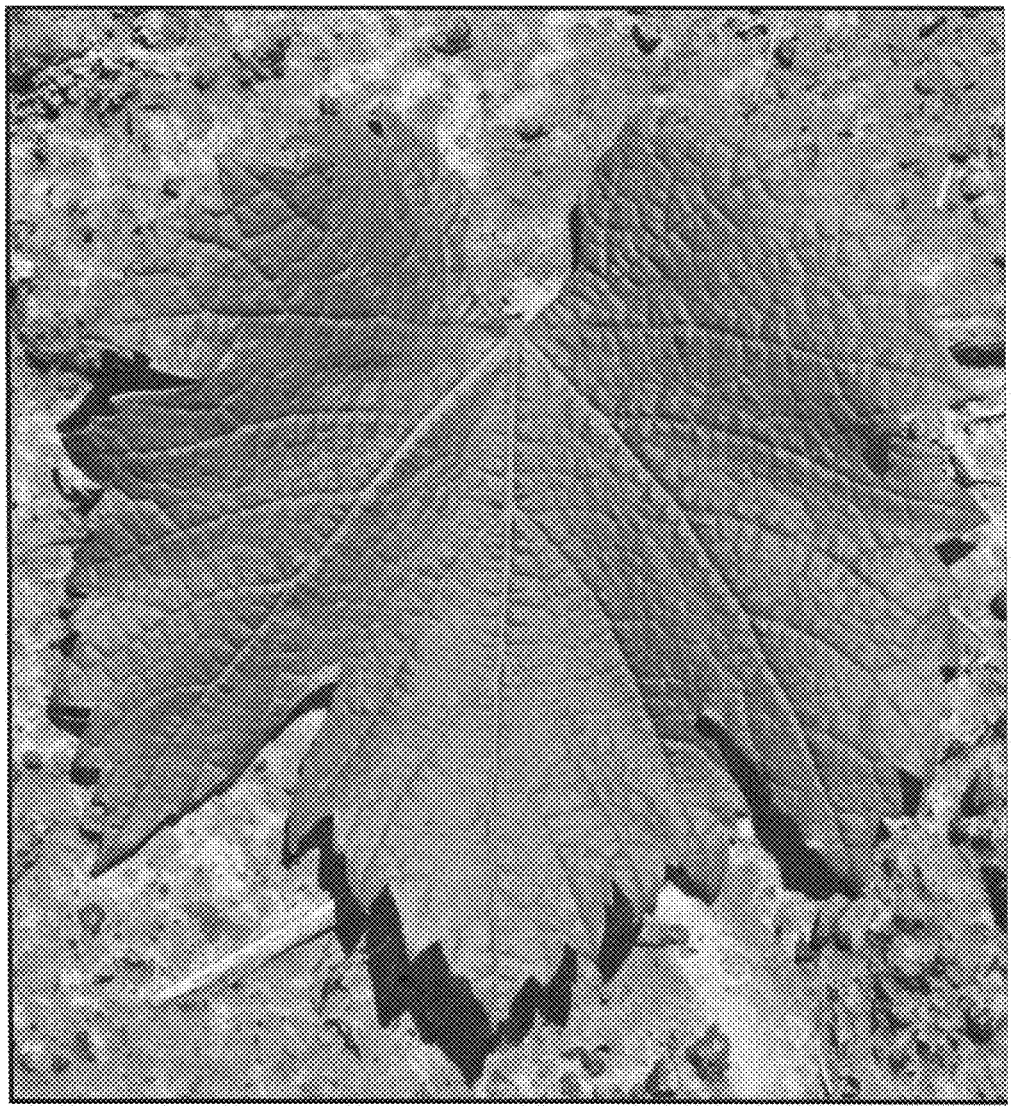
FIG. 4 is a photograph showing the upperside of a leaf of the plant.
Figure 5:
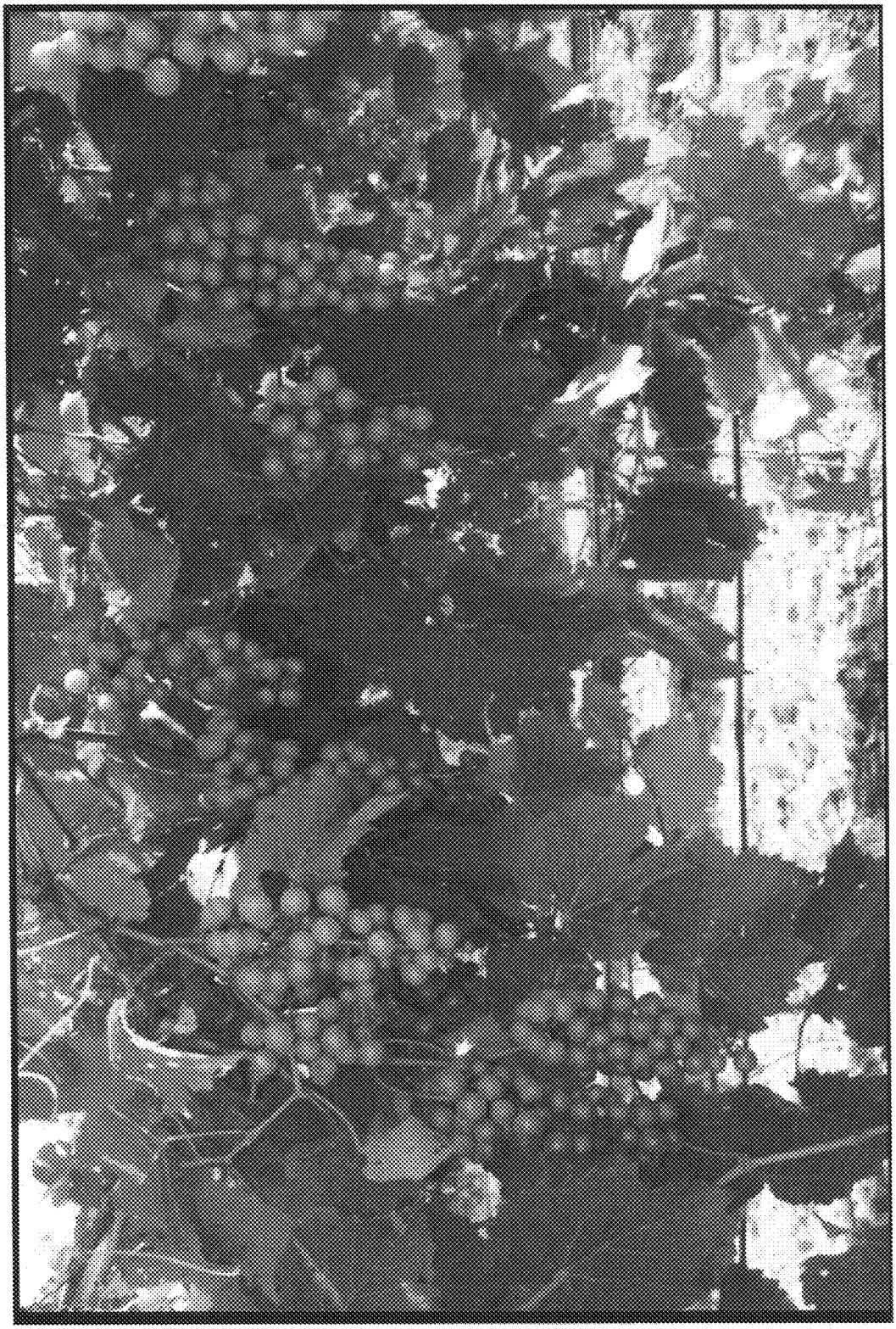
FIG. 5 is a photograph showing immature fruit on the plant.
Figure 6:
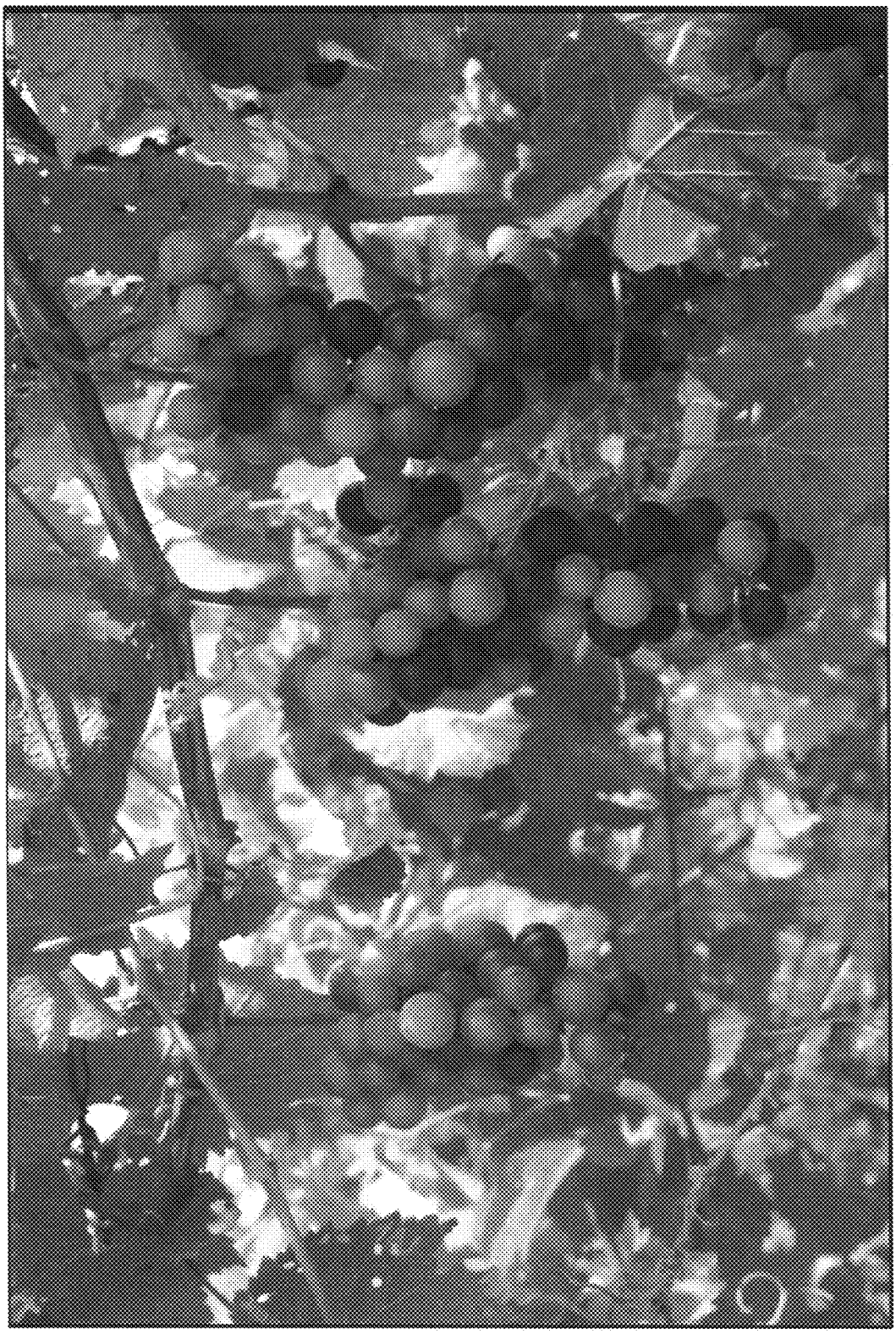
FIG. 6 is a photograph showing ripening fruit on the plant
Figure 7:
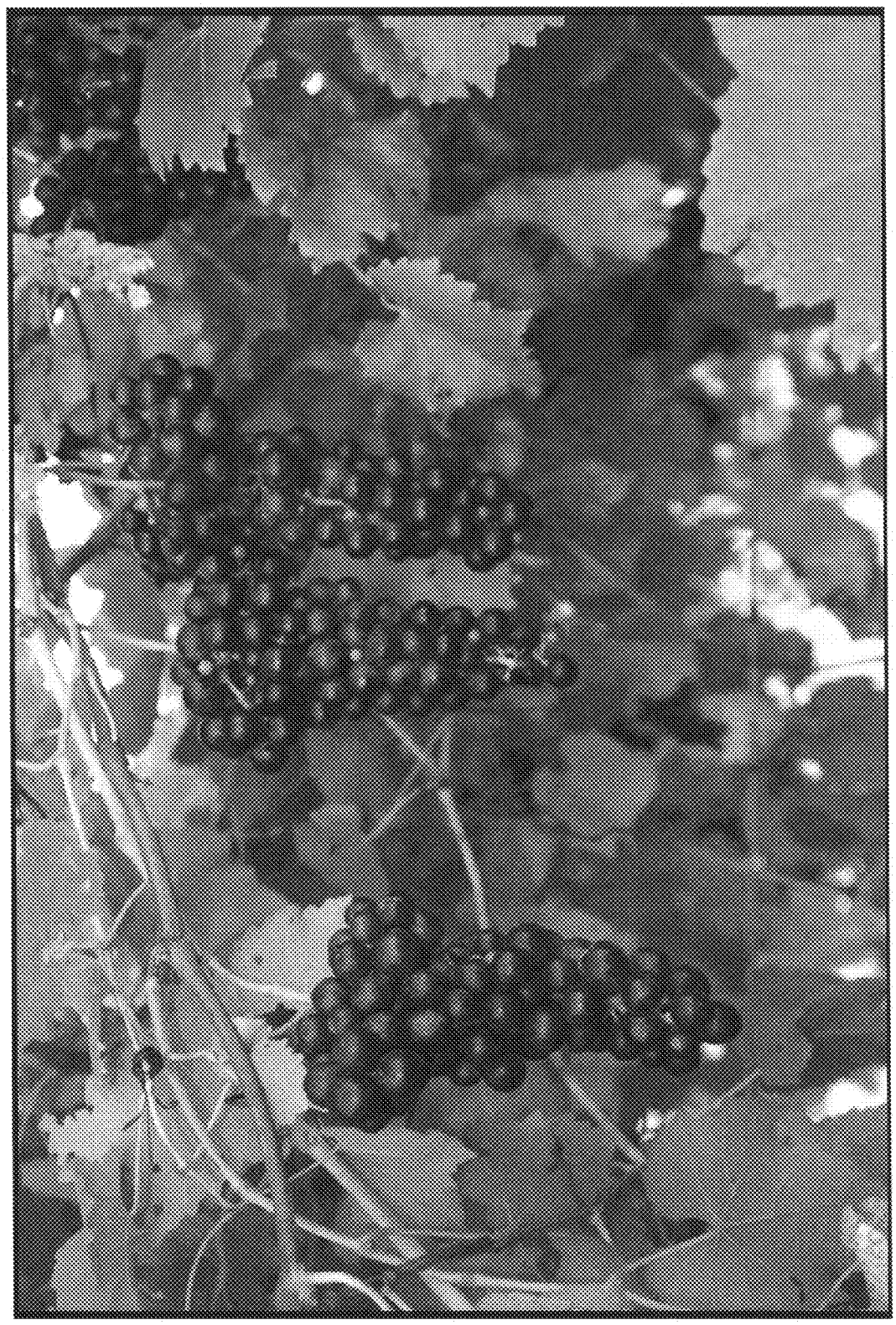
FIG. 7 is a photograph showing mature fruit on the plant.

Plants and fruits of this new cultivar differ phenotypically from its parents. The new cultivar is late ripening, demonstrates excellent plant health, extreme vigor, and excellent fruit quality for wine production.

The new variety has a perfect flower, as does "Cabernet Sauvignon"-unlike the "Munson" parent which has repressed stamens (which would make the plant not self-fertile.) The growth habit of the new variety is semi-drooping, in this case differing from both parents. "Munson" has a semi-erect growth habit, and "Cabernet Sauvignon" has a erect growth habit.

The new variety is moderately resistant to most common fungus diseases of grape vines. Under normal disease control programs, the vines and fruit have demonstrated good freedom from black rot [*Guignardia bidwellii* (*Ell.*) *V.* & *R.*], powdery mildew [*Uncinula necalor Burr.*], and downy mildew [*Plasmopora vilicola Berl.* & *Tomi.*]. Susceptibility to anthracnose [*Elsinoe ampelina* (*d By.*) (*Sher*)] is similar to that of Delaware, and is controlled by use of available fungicides. The fruit of the new variety has shown no inclination toward splitting following rains.

The date of ripening of the new variety is distinctly different from both parents. "Munson" (the female parent) ripens on the same date as "Cynthiana" (*Vitis aestivalis*). "Cabernet Sauvignon" (the male parent) ripens fifteen (15) days later than "Cynthiana." The new variety ripens twenty-nine (29) days later than "Cynthiana" and twelve (12) days before "Noble" (*Vitis rotundifolia*). Note: dates are taken from 2006 Harvest Records, Altus, Ark.

The fruit of the new variety has been used in juice and wine production, and has not been evaluated for cold storage nor shipping characteristics. Most berries adhere well to the fruit pedicel, however due to a tendency to ripen unevenly on the bunch, approximately 5% of the berries on a bunch may be subject to easy shattering because of over-ripeness.

The plant is also frost tolerant. Early in the 2007 growing season the ALTUS AVA (American Viticultural Area) experienced a devastating freeze event. On April $8^{th}$ low temperatures were 27° F. for 6 hours duration and on April $9^{th}$ the low temperatures were 26° F. for 11 hours duration. The Altus AVA bunch grape cultivars productivity was reduced to 0-10% of normal crop levels for the 2007 growing season. On April $27^{th}$ the Prophecy cultivar plants were evaluated for freeze damage. The scale of measure used for the evaluation was as follows: 1-10 with 1 being 0-10% viable buds and 10 being 90-100% viable buds. The 194-95 ('Prophecy') cultivar received a score of 8.5 (85% viable buds). The Chambourcin control cultivar in the same test row received a score of 1 (0-10% viable buds). Thus, 'Prophecy' is much more frost tolerant than other cultivars in the Altus AVA.

The following is a detailed description of the botanical and pomological characteristics of the subject grape. Color data are presented in Royal Horticultural Society Colour Chart designations. Where dimensions, sizes, colors and other characteristics are given, it is to be understood that such characteristics are approximations of averages set forth as accurately as practicable. Numbers are often presented as an average with the range of observations presented in parenthesis thereafter.

Plants used for botanical data were four or five years old and grown in a vineyard near Altus, Ark. For collection of the botanical data presented below the edition of The Royal Horticultural Society Colour Chart used was 1986, Edition No. 2.

Shoots/canes:

*Date of bud break.*—March 27th, Altus, Ark.

*Young shoots.*—26 cm (24-28) in length. Diameter at base 0.78 cm (0.69-0.88). Diameter at midpoint 0.52 cm (0.48-0.54). Diameter at terminal 0.24 cm (0.21-0.26). Internode length 7.79 cm (6.62-8.51). Shoot attitude: semi-drooping. Shoot color was not consistent Shaded side - yellow green group 146C. Sunlight side - greyed purple group 183A more red on sunlight exposed side. Anthocyanin was present on the sunlight exposed side

*Mature Canes* (*fall/winter*).—Diameter at base 1.04 cm (0.95-1.17). Diameter at midpoint 0.60 cm (0.50-0.68). Diameter at terminal 0.37 cm (0.28-0.42). Color at base greyed orange group 166D. Anthocyanin was not present. Color at midpoint greyed orange group 165D. Anthocyanin was not present. Color at terminal greyed orange group 164D. Anthocyanin was not present. Internode length at base 3.53 cm (2.72-5.16). Internode length at midpoint 6.23 cm (4.22-7.45). Internode length at terminal 6.14 cm (4.77-7.22). Lenticels were not present.

*Total cane length* (*average at end of season*).—352 cm (174-495).

*Pruning weight.*—6.86 lbs/vine — grown on Geneva Double Curtain (GDC).

*Vine height.*—238.76 cm (223.52-256.54). Trellis height was 182.88 cm and vine height above the trellis was 66.04 cm (48.26-86.36).

*Vine width.*—182.88 cm.

*Tendril* (*mature*) *pattern on shoot.*—2nd node was the first seen and the pattern was opposite nodes and constant. Total length 14.55 cm (10.7-20.0). Forked (y or n) yes. Color brown group 200A. Anthocyanin was present. Texture was smooth.

*Cane wood maturity at leaf fall.*—Shoot tips were not woody. Mostly mature. Growth habit was a combination of procumbent and upright. Procumbent (American type) on cordon. Upright (*V. vinifera* type) at head of plant.

Trunk: Four-year-old plants were measured at 20 cm above soil level to determine typical trunk diameter. Range was 42.0 mm-61.5 mm. Mean was 49.9 mm. Texture of the trunk was rough and peeling. Color of the trunk is Brown Group 200D.

Mature buds (compound buds):

*Average number of buds on a mature cane.*—82.8 (38-106).

*Dormant bud* (*eye*) *width*(*mm*) 4.9 mm (3.0-6.0).

*Shape.*—Spade (round point shovel).

*Color.*—Greyed orange group 166B.

*Texture.* —(smooth, etc) smooth.

Leaves: Simple and alternate. Shape is orbicular. Lobe number 5 shallow lobes. Petiole sinus is half-open. Venation palmate. Serrated margin. Rugose (rough texture-not smooth.). Teeth shape are convex. Teeth length are medium.

*Leaf length and width, without petiole.*—Length: 106.98 mm (range: 92.58 mm-113.63 mm). Width: 149.44 mm (range: 123.73 mm-166.28 mm).

*Color of the leaves.*—Young shoots base abaxial 146B yellow green. Anthocyanin was present in main and secondary veins. Young shoots base adaxial 137C green. Anthocyanin was not present. Young shoots midpoint abaxial 146B yellow green. Anthocyanin was present in main and secondary veins. Young shoots midpoint adaxial 137C green. Anthocyanin was present in main and secondary veins. Young shoots terminal abaxial 144A yellow green. Anthocyanin was present on sunlight half of leaf. Young shoots terminal adaxial 144A yellow green. Anthocyanin was present on sunlight half of leaf. Mature leaves base abaxial 146B yellow green. Anthocyanin was not present. Mature leaves base adaxial 137A green. Anthocyanin was present at point of origin of veins-extending 0.2 mm distal. Mature leaves midpoint abaxial 146B yellow green. Anthocyanin was not present. Mature leaves midpoint adaxial 137A green. Anthocyanin was not present. Mature leaves terminal abaxial 146B yellow green Anthocyanin was not present Mature leaves terminal adaxial 137A green. Anthocyanin was not present. Mature leaf abaxial vein Yellow-Green Group 146D Amount of pubescence on mature leaves sparse-erect. Present on: the Midrib, main veins and secondary veins. Petiole color of young leaves 141C green. Anthocyanin was present on the sunlight side of petiole. Pubescence on young leaves was very light. Present on: the Midrib, main veins and secondary veins.

*Petiole length and diameter.*—Length: 100.14 (range: 76.95 mm-108.87 mm). Width (measured at midpoint): 3.25 mm (range: 2.77 mm-3.64 mm).

*Petiole color of mature leaves.*—145A yellow green. Anthocyanin was present and continuous on adaxial half of petiole-most color at leaf end of petiole Pubescence on mature leaf petioles was sparse-erect

*Depth of sinus of mature leaf.*—2.82 cm (2.65-3.27).

*Width of sinus of mature leaf* (*widest point*).—2.88 cm (2.13-3.49). Sinus lobes are open Flowers/clusters:

*Date first bloom.*—May 9, 2007* *mean time of flowering.

*Date full bloom.*—May 15, 2007* when grown in Altus,

*Date last bloom.*—May 19, 2007* Ark.

*Stamen color.*—11C yellow.

*Stamen number.*—5.

*Pistil number.*—1.

*Pistil length.*—0.26 cm (0.25-0.28).

*Pistil color.*—144A yellow green.

*Petal color.*—N/A.

*Sepal.*—Number 5.

*Sepal color.*—144B yellow green.

*Pollen color.*—15B yellow orange.

*Individual flower dimensions.*—0.53 cm (0.50-0.58) Length and 0.55 cm (0.52-0.59) Width.

*Number of flowers per cluster.*—191 (159-279).

*Flower fragrance.*—Yes.

*Cluster shape.*—Cylindrical, usually not shouldered.

*Mature cluster length.*—9.46 cm (7.69-12.1) with peduncle.

*Mature cluster width.*—2.18 cm (1.99-3.54).

*Mature cluster weight.*—1.0 gm (0.6-1.3).

Fruit:

*Date ripe.*—09/10 through 09/24.

*Berry weight.*—1.86 gm.

*Berry diameter at equator.*—1.47 cm (1.34-1.62).

*Berry diameter at base.*—0.

*Berry diameter at apex* 0.—The berries are round.

*Berry length.*—1.47 cm (1.34-1.62).

*Berry shape.*—Round.

*Berry color.*—103A blue without bloom.

*Berry flesh color.*—Yellow group 11C, with minimal anthocyanin pigment blending into the flesh Skin thickness thin 0.02 cm. % SS 19.4 (2006) 13.7 (2007) 16 (2008). pH 3.3 (2006) 3.3 (2007) 3.27 (2008). Total acids 12.5 (2006) 11.5 (2007) 14.2 (2008). Berries/cluster 49.6 (22-72). Cluster/vine 169 (142-196) GDC and 99 (84-109) single curtain. Cluster/shoot 2-3. Seeds/berry 2.4 (1-3). Brush length 12.22 cm (6.37-14.81). Average peduncle length 4.16 cm (2.27-5.05). Pedicel length 0.61 cm (0.54-0.70). Pedicel diameter 0.17 cm (0.12-0.21). Pedicel color 144C yellow green. Pedicel texture smooth. Pedicel lenticels not abundant. Pedicel arrangement: 2 to 8 berries from a branched point of origin from the secondary branch from the rachis.

Seeds: Seed length range was 5.81 mm-6.78 mm. Mean was 6.45. Seed diameter range was 4.43 mm-5.24 mm. Mean was 7.75. Seed color was Brown Group 200D.

Productivity:

*Double curtain.*—(GDC) 12'×6' spacing, 11.66 lb/plt, 0.126 lb/cluster.

*Single curtain.*—(SC) 10'×7' spacing, 7.97 lb/plt, 0.092 lb/cluster.

The variety: The most distinctive features of the variety are its late ripening fruit, freeze tolerance, excellent plant health, extreme vigor, and excellent fruit quality for wine production.

We claim:

1. A new and distinct cultivar of grape plant named 'Prophecy', substantially as illustrated and described.

* * * * *